(12) United States Patent
Ferrari et al.

(10) Patent No.: US 7,060,838 B2
(45) Date of Patent: Jun. 13, 2006

(54) INDUSTRIAL PROCESS FOR THE SYNTHESIS OF ISOBUTYL METHYL 1,4-DIHYDRO-2,6-DIMETHYL-4-(2-NITROPHENYL)-3,5-PYRIDINE DICARBOXYLATE (NISOLDIPINE)

(75) Inventors: Massimo Ferrari, Cenate Sotto (IT); Marcello Ghezzi, Curno (IT); Manuel Alberelli, Grone (IT); Alberto Ambrosini, Lallio (IT)

(73) Assignee: Erregierre, S.P.A., San Paolo D'Argon (IT)

( * ) Notice: Subject to any disclaimer, the term of this patent is extended or adjusted under 35 U.S.C. 154(b) by 0 days.

(21) Appl. No.: 10/520,066

(22) PCT Filed: Jun. 26, 2003

(86) PCT No.: PCT/EP03/06755

§ 371 (c)(1), (2), (4) Date: Jan. 3, 2005

(87) PCT Pub. No.: WO2004/002958

PCT Pub. Date: Jan. 8, 2004

(65) Prior Publication Data

US 2005/0240022 A1    Oct. 27, 2005

(30) Foreign Application Priority Data

Jul. 1, 2002    (IT) ............................... MI02A1445

(51) Int. Cl.
*C07D 211/02* (2006.01)
(52) U.S. Cl. ........................................... 546/321
(58) Field of Classification Search ............ 546/321
See application file for complete search history.

(56) References Cited

U.S. PATENT DOCUMENTS 4,154,839 A    5/1979  Wehinger et al.
4,600,778 A    7/1986  Teller et al.

*Primary Examiner*—Patricia L. Morris
(74) *Attorney, Agent, or Firm*—Gifford, Krass, Groh, Sprinkle, Anderson & Citkowski, P.C.

(57) ABSTRACT

Synthetic process of isobutyl methyl 1,4,-dihydro-2,6-dimethyl-4-(2-nitrophenyl)3,5-pyridine dicarboxylate (Nisoldipine) comprising on the reaction of isobutyl 2-(2-nitrobenzylidene)acetoacetate with methyl 3-aminocrotonate in an apolar solvent.

6 Claims, No Drawings

INDUSTRIAL PROCESS FOR THE SYNTHESIS OF ISOBUTYL METHYL 1,4-DIHYDRO-2,6-DIMETHYL-4-(2-NITROPHENYL)-3,5-PYRIDINE DICARBOXYLATE (NISOLDIPINE)

FIELD OF THE INVENTION

The present invention refers to a process for the synthesis of isobutyl methyl 1,4-dihydro-2,6-dimethyl-4-(2-nitrophenyl)-3,5-pyridine dicarboxylate (Nisoldipine).

PRIOR ART

Nisoldipine is a substance pharmacologically active as calcium antagonist and antihypertensive.

Nisoldipine synthesis processes are known in the art, e.g. those disclosed in patents U.S. Pat. No. 4,154,839 and U.S. Pat. No. 4,600,778.

Said patents describe synthetic routes leading to the formation, as Nisoldipine's characteristic impurities, of the dimethylester derivative (dimethyl 1,4-dihydro-2,6-dimethyl-4-(2-nitrophenyl)-3,5-pyridine dicarboxylate: impurity A) and of the diisobutyl ester derivative (diisobutyl 1,4-dihydro-2,6-dimethyl-4-(2-nitrophenyl)-3,5-pyridine dicarboxylate: impurity E).

In particular, basic patent U.S. Pat. No. 4,154,839 discloses that said preparation is carried out in an alcoholic solvent, but does not specify the Nisoldipine chromatographic purity obtained.

Tests carried out by the Applicant according to the process disclosed in U.S. Pat. No. 4,154,839 (Example 1) showed an impurities content of the order of 3% (as concerns impurity A) and 2% (as concerns impurity E).

Considering the great similarity between said impurities and Nisoldipine, it is very difficult to purify Nisoldipine from them. It follows that the aforesaid yield does not correspond to the real yield of the purified final product, obtained by complex techniques and in any case causing a product loss in respect of the crude product obtained.

Therefore, the need was deeply felt for a new Nisoldipine synthesis process giving a final product of high purity especially as concerns the two Nisoldipine's characteristic impurities, i.e. the dimethyl ester derivative (A) and the diisobutyl ester derivative (E), and easily exploitable on a commercial scale, being based on the use of low-cost and commercially available reagents and not requiring the crude Nisoldipine purification, which is complex, costly and entails an increase in yield losses.

SUMMARY

A new process for Nisoldipine synthesis free from the drawbacks of the processes known is the art has now been found.

The Applicant has surprisingly and unexpectedly found a new process for the synthesis of isobutyl methyl 1,4-dihydro-2,6-dimethyl-4-(2-nitrophenyl)-3,5-pyridine dicarboxylate (Nisoldipine) comprising the reaction of isobutyl 2-(2-nitrobenzylidene)acetoacetate with methyl 3-aminocrotonate in an apolar solvent, e.g. aliphatic or cycloaliphatic solvents, in particular cyclohexane and/or n-hexane, to give crude Nisoldipine, whose purification by simple crystallisation from an acetone/water mixture yields a Nisoldipine final product of high purity (>99.5%, by HPLC), especially as concerns the two Nisoldipine's characteristic impurities, i.e. the dimethyl ester derivative (A) and the diisobutyl ester derivative (E).

The crude Nisoldipine obtained according to the present invention can be converted into a high-purity Nisoldipine final product by a simple purification method, such as the crystallisation, since the degree of purity of the aforesaid crude Nisoldipine already exceeds 99% (by HPLC).

DETAILED DESCRIPTION OF THE INVENTION

It is therefore an object of the present invention to provide a process for the synthesis of isobutyl methyl 1,4-dihydro-2,6-dimethyl-4-(2-nitrophenyl)-3,5-pyridine dicarboxylate (Nisoldipine) comprising the reaction of isobutyl 2-(2-nitrobenzylidene)acetoacetate with methyl 3-aminocrotonate, added to the reaction mixture in one single portion or portionwise, in the presence or in the absence of 4-dimethyl aminopyridine, in an apolar solvent, e.g. aliphatic or cycloaliphatic solvents, in particular cyclohexane and/or n-hexane, to give crude Nisoldipine, isolated directly from the reaction solvent or by filtration from a water/methanol mixture, after elimination of the reaction solvent by distillation.

The crude Nisoldipine obtained through the reaction described above is over 99% pure (by HPLC) and is purified by simple crystallisation from water and a water soluble solvent mixture, in particular an acetone/water mixture to give a Nisoldipine final product with a high degree of purity (>99.5% by HPLC), especially as concerns the content of two Nisoldipine's characteristic impurities, i.e. the dimethyl ester derivative (A) and the diisobutyl ester derivative (E).

In a preferred embodiment of the Nisoldipine synthesis process being the object of the present invention, after reaction of isobutyl 2-(2-nitrobenzylidene)acetoacetate with methyl 3-aminocrotonate in an apolar solvent to give crude Nisoldipine, said Nisoldipine is purified by crystallisation from water and a water soluble solvent mixture, in particular an acetone/water mixture, to give a pure Nisoldipine final product.

In a further preferred embodiment of the present invention, before the reaction of isobutyl 2-(2-nitrobenzylidene)acetoacetate with methyl 3-aminocrotonate, as described above, said Nisoldipine synthesis intermediate, i.e. isobutyl 2-(2-nitrobenzylidene)acetoacetate, is obtained by reacting 2-nitrobenzaldehyde with isobutyl acetoacetate in methylene chloride, as solvent, in the presence of a catalytic amount of piperidine formate at a temperature of –10° C. to 50° C., preferably of 20° C. to 50° C., more preferably of 27° C. to 33° C.

The catalyst, piperidine formate, forms in situ in the reaction mixture by addition of equimolar amounts of formic acid and piperidine.

The amount of catalyst, piperidine formate, used is 0.05–0.7 mol catalyst/mol 2-nitrobenzaldehyde, preferably 0.05–0.6 mol catalyst/mol 2-nitrobenzaldehyde, more preferably 0.25 mol catalyst/mol 2-nitrobenzaldehyde.

In a preferred embodiment of the invention, the intermediate obtained, i.e. isobutyl 2-(2-nitrobenzylidene)acetoacetate, is isolated in the presence of aqueous acetic acid as solvent.

Said process of synthesis of isobutyl 2-(2-nitrobenzylidene)acetoacetate, an intermediate of Nisoldipine synthesis, is a valid alternative, easily exploitable on a commercial scale, to the processes of synthesis of said intermediate known in the art.

The following examples are conveyed by way of indication, not of limitation, of the present invention.

EXPERIMENTAL PART

EXAMPLE 1

Synthesis of isobutyl 2-(2-nitrobenzylidene)acetoacetate

A reactor was fed with 2-nitrobenzaldehyde (18 kg; 0.119 kmol) and methylene chloride (36 kg). The resultant mixture was heated to 27°–33° C., added with isobutyl acetoacetate (19.8 kg; 0.125 kmol), and successively, with piperidine (2.62 kg; 0.03 kmol) and 99% formic acid (1.43 kg; 0.03 kmol). The temperature of 27°–33° C. was maintained for a period of 20 hrs. After that time, distilled water (9 kg) was added. The lower organic phase was separated and the aqueous phase was eliminated.

The organic phase was concentrated in plenum at an internal temperature of 65° C. max. The reactor was put under vacuum while distillation was continued at an internal temperature of 50° C. max for a period of 1 hr at least, in any case until the mass precipitated. The residue so obtained was treated with 80% acetic acid (3 kg) at 40°–50° C. and stirred at said temperature until complete dissolution. The solution obtained was cooled to 25°–30° C. for a period of 1 hr at least, until complete precipitation. The temperature was lowered to 0°–5° C. for at least 2 hrs. Then centrifugation was performed and the precipitate was washed with 80% acetic acid (18 kg) and then with distilled water (54 kg). The solid was dried at 40°–50° C. to give 22 kg of dried isobutyl 2-(2-nitrobenzylidene)acetoacetate. Yield: 63.4 %.

EXAMPLE 2

Synthesis of Nisoldipine

A reactor was fed with isobutyl 2-2(nitrobenzylidene) acetoacetate (22 kg; 0.0755 kmol), 4-dimethylaminopyridine (0.55 kg), methyl 3-aminocrotonate (6.1 kg; 0.053 kmol), cyclohexane (88 kg). The mass was refluxed (75°–85° C.) for a period of 10 hrs, then an additional amount of methyl 3-aminocrotonate (6.1 kg) was added. The reaction mass was refluxed (75°–85° C. ) for 16 hrs at least (during the reaction the product precipitated).

Distillation was performed in plenum at an internal temperature of 85° C. max, until formation of a pasty but stirrable residue. The residue was cooled to 20°–30° C.; distilled water (11 kg) and methanol (66 kg) were added. The mixture was stirred at 20°–30° C. for a period of 15 min, cooled to 10°–15° C. with stirring for 30 min at least, centrifuged and washed with methanol (16.5 kg) and then with distilled water (16.5 kg). The wet solid obtained (crude Nisoldipine) was fed to a rector, added with acetone (77 kg), stirred at 20°–30° C. until dissolution, added with distilled water (40.5 kg), kept under stirring at 20°–30° C. for 1 hr at least, until complete precipitation. An additional amount of distilled water (9.5 kg) was added at 20°–25° C. The mixture was maintained under stirring at 20°–25° C. for an additional 1 hr and centrifuged. The final solid was washed with an acetone (16.5 kg)/distilled water (16.5 kg) mixture prepared separately, and then with distilled water (22 kg). The solid was dried at 40°–50° C. to give 15.5 kg dried Nisoldipine product with a degree of purity of over 99.7% (HPLC). Yield 52.9%.

The invention claimed is:

1. Process for the synthesis of isobutyl methyl 1,4-dihydro-2,6-dimethyl-4-(2-nitrophenyl)-3,5-pyridine dicarboxylate (Nisoldipine) based on the reaction of isobutyl 2-(2-nitrobenzylidene)acetoacetate with methyl 3-aminocrotonate, added to the reaction mixture at a time or portionwise, in non-polar solvent, to give crude Nisoldipine.

2. The process as claimed in claim 1, wherein the non-polar solvent is selected from the group consisting of aliphatic or cycloaliphatic solvents.

3. The process as claimed in claim 2, wherein the solvent is selected from the group consisting of cyclohexane and/or n-hexane.

4. The process as claimed in claim 1, wherein the reaction of isobutyl 2-(2-nitrobenzylidene)acetoacetate and methyl 3-aminocrotonate is carried out in the presence of 4-dimethylaminopyridine.

5. The process as claimed in claim 1, wherein, downstream of the reaction of isobutyl 2-(2-nitrobenzylidene) acetoacetate with methyl 3-aminocrotonate in a non-polar solvent to give crude Nisoldipine, said Nisoldipine is purified by crystallisation from a water/water soluble solvent mixture to give a pure Nisoldipine final product.

6. The process as claimed in claim 5, wherein the water/water soluble solvent mixture is acetone/water.

* * * * *